United States Patent [19]

Bitha et al.

[11] Patent Number: 4,996,337

[45] Date of Patent: Feb. 26, 1991

[54] SYNTHESIS OF CISPLATIN ANALOGS

[75] Inventors: Panayota Bitha, Pomona; Joseph J. Hlavka, Tuxedo Park; Yang-I Lin, Tappan, all of N.Y.

[73] Assignee: American Cyanamid Company, Wayne, N.J.

[21] Appl. No.: 493,043

[22] Filed: Mar. 13, 1990

Related U.S. Application Data

[62] Division of Ser. No. 281,376, Dec. 8, 1988, Pat. No. 4,937,358, which is a division of Ser. No. 65,441, Jun. 23, 1987, Pat. No. 4,808,730.

[51] Int. Cl.$^5$ .................. C07F 17/02; A61K 31/555; A61K 31/28

[52] U.S. Cl. .................. 556/137; 549/206; 546/5; 546/11; 548/402; 556/40

[58] Field of Search .................. 556/137, 136, 40; 549/206; 546/5, 11, 12; 548/403, 402; 514/492

[56] References Cited

U.S. PATENT DOCUMENTS

| | | | |
|---|---|---|---|
| 4,845,124 | 7/1989 | Kidani et al. | 514/492 |
| 4,882,447 | 11/1989 | Tsujihara et al. | 556/40 |
| 4,921,984 | 5/1990 | Nowatari et al. | 556/40 |

*Primary Examiner*—Arthur C. Prescott
*Attorney, Agent, or Firm*—Kenneth J. Dow

[57] ABSTRACT

This disclosure sets forth a novel process for producing cisplatin analogs which possess antitumor activity.

2 Claims, No Drawings

SYNTHESIS OF CISPLATIN ANALOGS

CROSS REFERENCE TO RELATED APPLICATION

This is a divisional of application Ser. No. 281,376, filed on Dec. 8, 1988, now U.S. Pat. No. 4,937,358, which is a divisional of application Ser. No. 065,441, filed June 23, 1987, now U.S. Pat. No. 4,808,730.

DESCRIPTION OF THE INVENTION

This invention is concerned with a process for producing compounds of formula I:

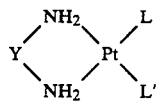

Formula I wherein Y is selected from the group consisting of:

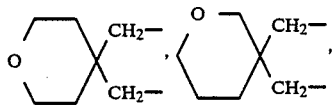

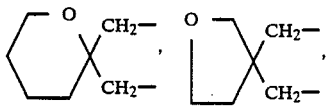

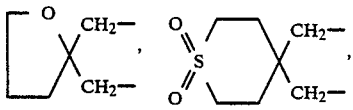

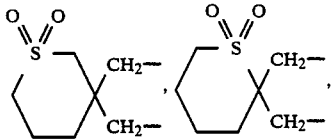

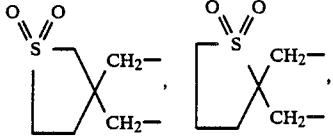

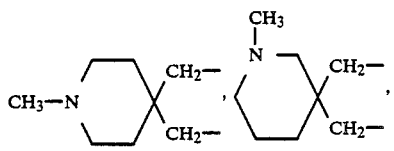

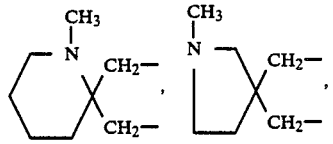

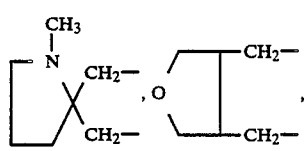

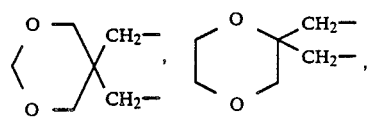

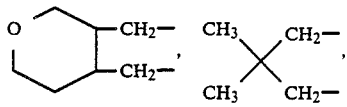

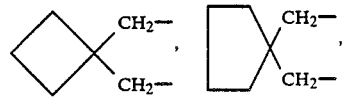

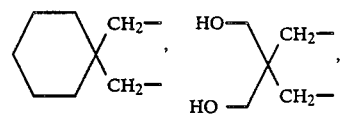

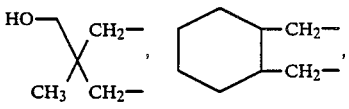

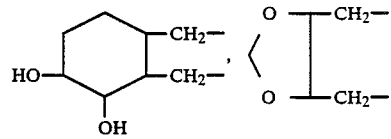

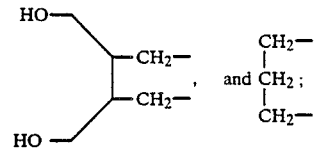

and L and L' are monobasic carboxylates selected from the group consisting of acetate, hydroxyacetate and propionate, or L and L' taken together are a dibasic carboxylate selected from the group consisting of

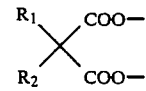

wherein $R_1$ and $R_2$ are hydrogen or lower alkyl($C_1$–$C_5$) or $R_1$ and $R_2$ taken together is —$(CH_2)_n$— where n is 2 to 5 and moieties of the formulae:

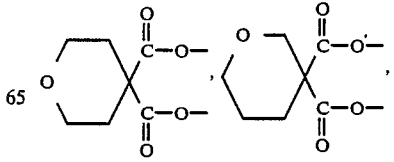

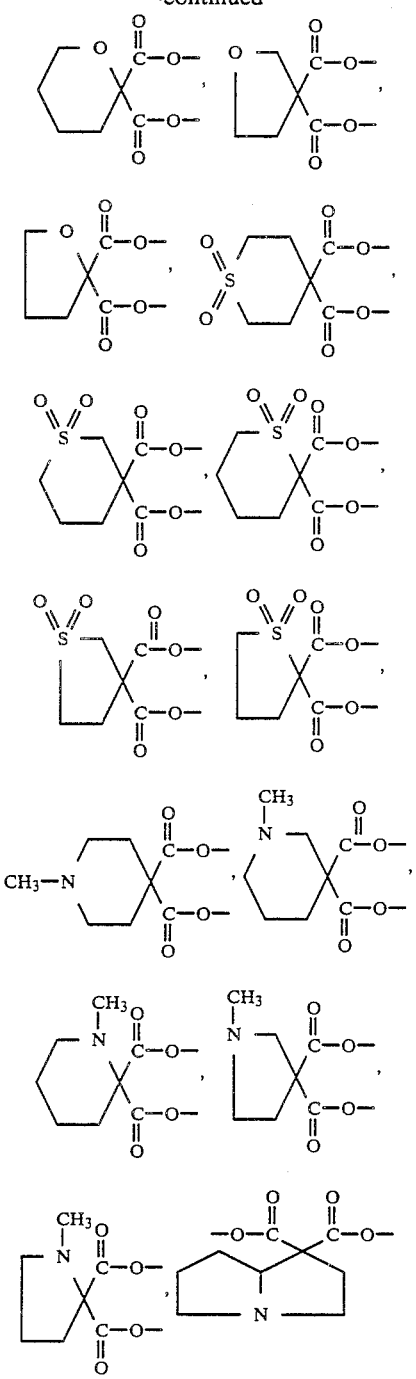

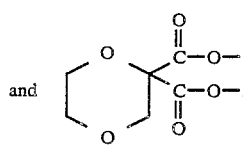

The compounds described in Formula I are highly active antitumor agents. Their activity as such has been disclosed in U.S. patent applications Ser. No. 6/819,164, filed Jan. 15, 1986 and Ser. No. 6/824,404, filed Jan. 31, 1986 and in U.S. Pat. No. 4,760,157.

The process with which the current invention is concerned is described below by flowchart and text.

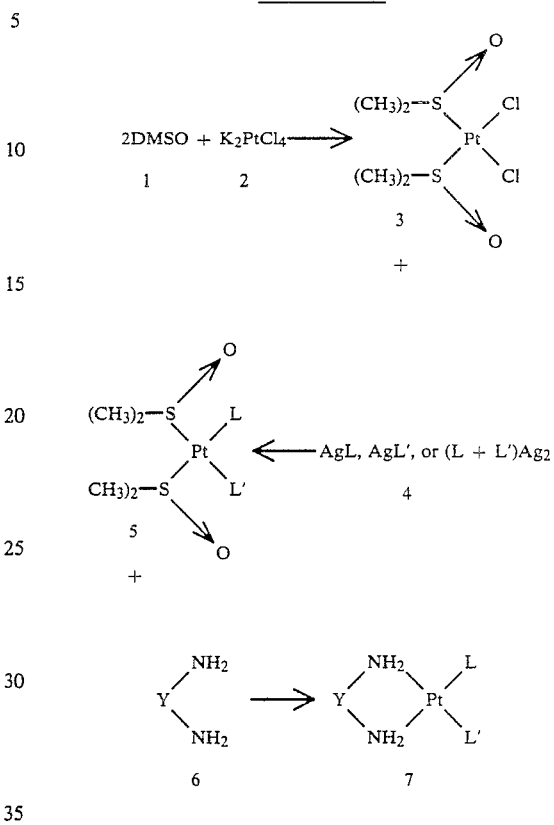

In accordance with flowchart A, dimethyl sulfoxide 1 is reacted with potassium tetrachloroplatinate 2 in aqueous solution to produce sulfinyl bismethane, compound with platinum dichloride (2:1) 3. Compound 3 is then reacted with a mono- or dicarboxylic acid silver salt (L, L' or L+L')4 in aqueous solution, protected from light, giving carboxylic acid-bis[sulfinylbis[methane]-S]platinum derivative 5. Compound 5 is then reacted with an amine 6 giving the final, pharmacologically active product 7 (Formula I)

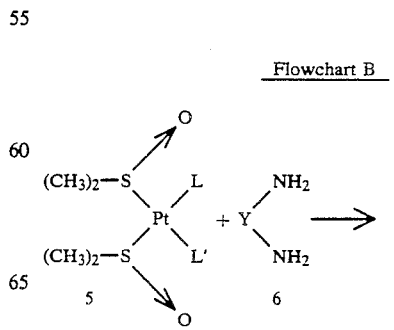

-continued
Flowchart B

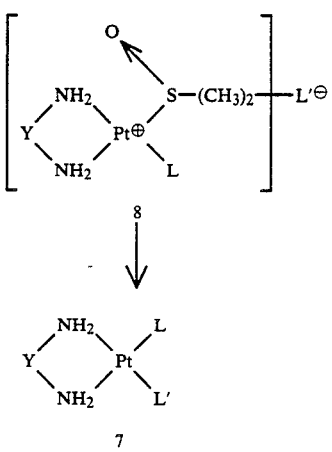

In accordance with Flowchart B, a carboxylic acid-bis[sulfinylbis[methane]-S]platinum derivative 5 is reacted with an amine 6, giving an amine, carboxylic acid [sulfinylbis[methane]-S]platinum derivative 8, which on heating in aqueous solution gives the biologically active derivative 7.

The intermediates 5 and 8 are unknown in the art and since they are integral in the preparation of pharmaceutically useful products, they will be claimed as new compounds as a part of this invention.

The invention will be described further in conjunction with the following specific examples.

EXAMPLE 1

[1,1-Cyclobutanedicarboxylato(2-)-O,O¹]bis[sulfinylbis[methane]-S]platinum

To a solution of 41.5 g of potassium tetrachloroplatinate in 330 ml of water was added 21.3 ml of dimethyl sulfoxide. The mixture was allowed to stand 12 hours, then the solid was collected, washed with water, ethanol and ether, giving 38.0 g of sulfinyl bismethane, compound with platinum chloride (2:1), mp 222° C. (dec.).

A mixture of 12.66 g of the above compound, 10.74 g of the disilver salt of 1,1-cyclobutanedicarboxylic acid and 900 ml of water was stirred in the dark for 22 hours and then filtered. The filtrate was concentrated to 40 ml and the precipitate collected, giving 12.4 g of [1,1-cyclobutanedicarboxylato(2-)-O,O¹]bis[sulfinylbis[methane]-S]platinum, mp 208° C. (dec.).

This compound (494 mg) in a hot solution of 12 ml of water, was reacted with a hot solution of 114 mg of trans-(−)-1,2-cyclohexandiamine in 3 ml of water. The mixture was kept at 100° C. for 6 hours, then cooled, giving 360 mg of biologically active trans-(−)-1,2-cyclohexanediamine, compound with [1,1-cyclobutanedicarboxylato(2-)-O,O¹]platinum (1:1).

EXAMPLE 2

Preparation of
[1,1-Cyclobutanedicarboxylato(2-)-O,O¹](1,3-dioxane-5,5-dimethanamine-N,N')platinum A suspension of 26.2 g of 2,2-bis(bromomethyl)-1,3-propanediol, 50 ml of concentrated hydrochloric acid and 50 ml of 38% formaldehyde was stirred in a 50° C. oil bath overnight, then cooled to room temperature and filtered. The filtrate was extracted with three 100 ml portions of ether. The ether extracts were combined, washed with water, dried and evaporated to an oil. A small amount of solid which formed was removed by filtration and washing with ether. The combined filtrate and wash was evaporated under reduced pressure, giving 26.9 g of 5,5-bis(bromomethyl)-1,3-dioxane as a clear oil.

A suspension of 2.69 g of 5,5-bis(bromomethyl)-1,3-dioxane, 3.8 g of sodium azide and 50 ml of dimethylformamide was heated at 130° C. in an oil bath overnight, then cooled and filtered. The filtrate was evaporated to an oily suspension which was diluted with 30 ml of water. The oily phase was extracted with three 25 ml portions of ether. The ether extracts were combined, dried and evaporated, giving 1.95 g of 5,5-bis(azidomethyl)-1,3-dioxane.

A mixture of 1.95 g of 5,5-bis(azidomethyl)-1,3-dioxane, 0.5 g of 10% palladium on calcium carbonate and 40 ml of ethanol was reduced for 2 hours and then filtered. The filtrate was evaporated, giving 1.41 g of 1,3-dioxane-5,5-dimethanamine as an oil.

A 1.97 g portion of [1,1-cyclobutanedicarboxylato(2-)-O,O¹]bis[sulfinylbis[methane]-S]platinum was dissolved in 48 ml of hot (100° C.) water. To this was added a solution of 585 mg of 1,3-dioxane-5,5-dimethanamine in 12 ml of water. The mixture was stirred at 100° C. for 6 hours and then evaporated to dryness. The residue was dissolved in 2 ml of hot water and filtered. The filtrate was cooled, then refrigerated for 2 hours and the solid collected, giving 606 mg of biologically active [1,1-cyclobutanedicarboxylato(2-)-O,O¹](1,3-dioxane-5,5-dimethanamine-N,N')platinum.

EXAMPLE 3

Preparation of [1,1 Cyclobutanedicarboxylato(2-)-O¹,O¹](tetrahydro-4H-pyran-4,4-dimethanamine-N,N')platinum A mixture of 28.6 g of dichloroethyl ether, 13.2 g of malononitrile, 55.28 g of potassium carbonate and 800 ml of acetonitrile was refluxed on a steam bath for 24 hours, then filtered while hot. The filtrate was evaporated and the residue crystallized, with charcoal treatment, from 100 ml of ethanol, giving 9.5 g of tetrahydro-4H-pyran-4,4-dicarbonitrile as colorless plates, mp 110°-112° C.

A 180 ml portion of 1N borane in tetrahydrofuran was added rapidly, dropwise to a solution of 8.18 g of tetrahydro-4H-pyran-4,4-dicarbonitrile in 150 ml of tetrahydrofuran. This mixture was warmed, then cooled to room temperature in an ice bath and then stirred for 64 hours at room temperature. A 100 ml portion of ethanol was added dropwise, then the mixture was stirred 4 hours and evaporated to dryness. The residue was taken up in 100 ml of water, acidified with 50 ml of 6N hydrochloric acid and extracted three times with ether. The remaining aqueous layer was evaporated to dryness. The residue was boiled in 300 ml of methanol and filtered while hot. The filtrate was treated with 200 ml of ether and cooled. The resulting solid was collected, washed with ether and dried, giving 8.31 g of tetrahydro-4H-pyran-4,4-dimethanamine, dihydrochloride.

An ion exchange resin (Dowex, 1-X4) was slurried in 10N sodium hydroxide and then packed into a ¾ inch column. The column was washed with water until the pH was neutral. An aqueous solution of 2.17 g of tetrahydro-4H-pyran-4,4-dimethanamine, dihydrochloride was added to the column at a slow flow rate. The column cut containing the free base was evaporated, giving 1.48 g of tetrahydro-4H-pyran-4,4-dimethanamine as a colorless oil.

A 4.9 g portion of [1,1-cyclobutanedicarboxylato(2-)-O,O¹]bis[sulfinylbis[methane]-S]platinum was dissolved in 120 ml of water at 100° C. A solution of 1.4 g of tetrahydro-4H-pyran-4,4-dimethanamine in 30 ml of water was added and the mixture was heated at 100° C. for 6 hours. The mixture was filtered and the filtrate evaporated to dryness. The residue was slurried in 30 ml of water, heated to 95° C. and filtered. The filtrate was concentrated to about 10 ml and the resulting solid collected, washed with water and dried, giving 1.34 g of biologically active [1,1-cyclobutanedicarboxylato(2-)-O¹,O¹](tetrahydro-4H-pyran4,4-dimethanamine-N,N']platinum.

EXAMPLE 4

Preparation of [2,2-Bis(aminomethyl)-1,3-propanediol-N,N'][1,1-cyclobutanedicarboxylato(2-)-O¹,O¹]platinum To a solution of 1.0 g of [1,1-cyclobutanedicarboxylato(2-)-O,O¹]bis[sulfinylbis[methane]-S]platinum in 25 ml of water at 100° C. was added a solution of 272 mg of 2,2-bis(aminomethyl)-1,3-propanediol in 5 ml of water. The mixture was heated at 100° C. for 6 hours and then filtered. The filtrate was evaporated to about 3 ml and the resulting solid collected, giving 100 mg of biologically active [2,2bis(aminomethy)-1,3-propanediol-N,N'][1,1-cyclobutanedicarboxylato(2-)-O¹,O¹]-platinum.

EXAMPLE 5

Preparation of 2,2-Dimethyl-1,3-propanediamine, compound with [11--cyclobutanedicarboxylato(2-)-O,O¹]platinum To a warm solution of 1.24 g of [1,1-cyclobutanedicarboxylato(2-)-O,O¹]bis[sulfinylbis[methane]-S]platinum in 60 ml of water was added 0.26 g of 2,2-dimethyl-1,3-propanediamine. The mixture was kept at 100° C. for 20 hours and then evaporated under reduced pressure. The residue was recrystallized from 10 ml of water, giving 510 mg of biologically active 2,2-dimethyl-1,3-propanediamine, compound with [1,1-cyclobutanedicarboxylato(2-)-O,O¹]platinum.

EXAMPLE 6

Bis(Acetato-O)bis[sulfinylbis[methane]-S]platinum

A 20.75 g portion of potassium tetrachloroplatinate was added to 165 ml of water, stirred for a few minutes and then filtered. To the filtrate was added 10.65 g of dimethyl sulfoxide. The suspension was allowed to stand for 14 hours, then the crystals were collected, washed with water, ethanol and ether and dried, giving 18.57 g of sulfinylbismethane, compound with platinum chloride.

A suspension of 1.27 g of sulfinylbismethane, compound with platinum chloride, 1.0 g of silver acetate and 70 ml of water was stirred in the dark overnight, then filtered and the filtrate evaporated to dryness. The residue was slurried in methanol, diluted with ether and the solid collected and dried, giving 1.2 g of bis(acetato-O)-bis[sulfinylbis[methane]-S]platinum.

EXAMPLE 7

Propanedioato(2-)-O¹,O³]bis[sulfinylbis[methane]S]-platinum

A suspension of 1.27 g of sulfinylbismethane, compound with platinum chloride, 953 mg of the disilver salt of malonic acid and 70 ml of water was stirred in the dark overnight, then filtered and the filtrate evaporated to dryness. The residue was slurried in methanol, diluted with ether and the solid collected and dried, giving 1.15 g of [propanedioato(2-)-O¹,O³]bis[sulfinylbis[-methane]-S]-platinum.

EXAMPLE 8 trans-(—)-[1,1-Cyclobutanedicarboxylato(2-)-O,O¹]-(1,2-cyclohexanediamine-N,N')[sulfinylbis[methane]-S]platinum To a solution of 1.24 g of [1,1-cyclobutanedicarboxylato(2-)-O,O¹]bis[sulfinylbis[methane]-S]platinum in 40 ml of water at 40° C. was added 285 mg of trans-(—)-1,2-cyclohexanediamine. The mixture was heated at 40° C. for 1 hour, then evaporated at 40° C. under reduced pressure. The residue was triturated with ethanol and ether, giving 1.15 g of trans-(—)-[1,1-cyclobutanedicarboxylato(2-)-O,O¹](1,2-cyclohexanediamine-N,N')[sulfinylbis[methane]-S]platinum.

A 200 mg portion of the above compound in 5 ml of water was heated at 100° C. for 6 hours, then cooled and the solid collected and dried, giving 130 mg of biologically active trans-(—)-1,2-cyclohexanediamine, compound with [1,1-cyclobutanedicarboxylato(2-)-O,O¹]-platinum.

We claim:

1. A compound of the formula:

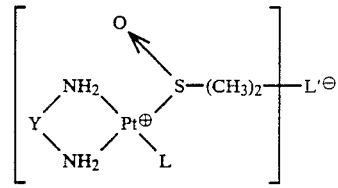

wherein Y is selected from the group consisting of

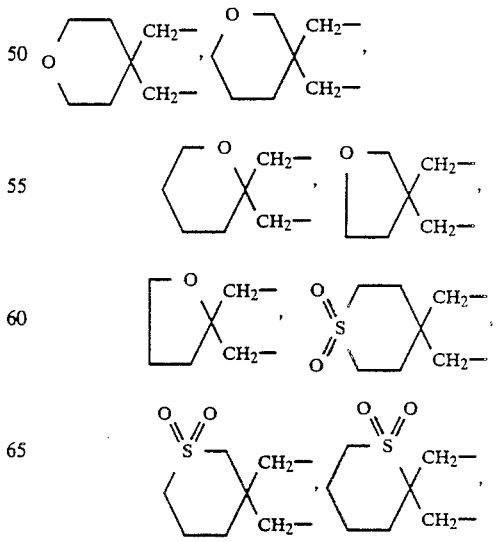

-continued
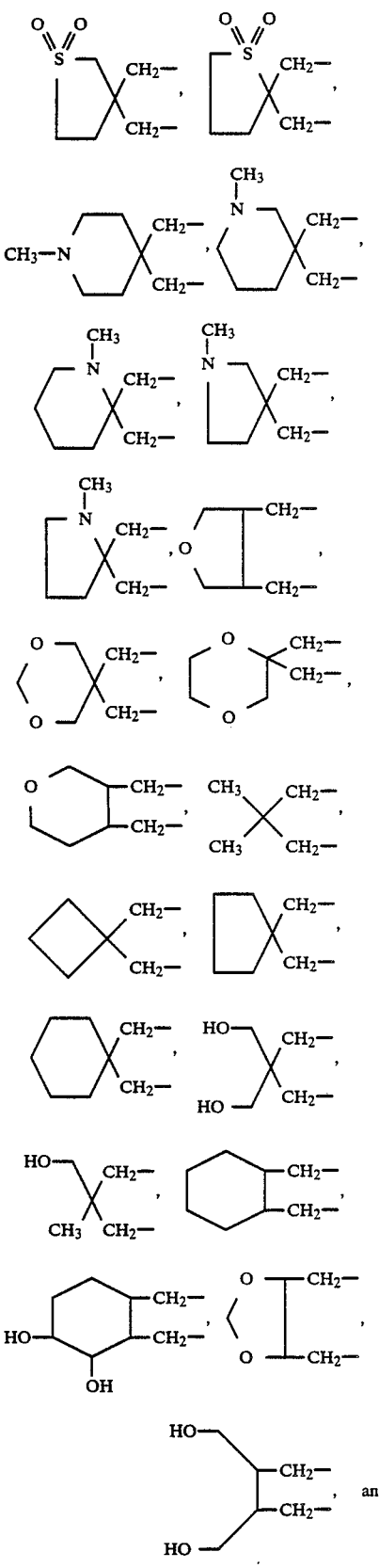
and L and L' are monobasic carboxylates selected from the group consisting of acetate, hydroxyacetate and propionate, or L and L' taken together are a dibasic carboxylate selected from the group consisting of
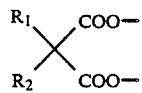
where $R_1$ and $R_2$ are hydrogen or lower alkyl($C_1$–$C_5$) or $R_1$ and $R_2$ taken together is —$(CH_2)_n$— where n is 2 to 5 and moieties of the structure:
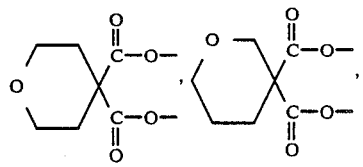
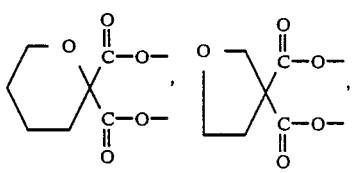
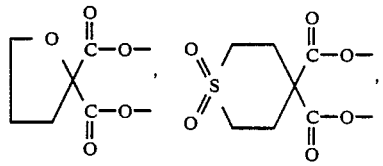
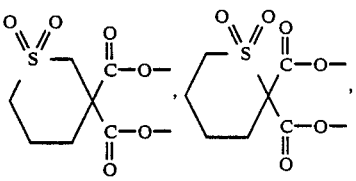
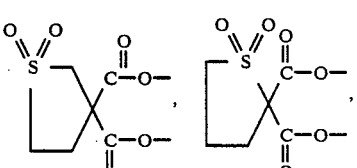
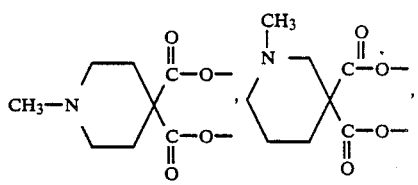
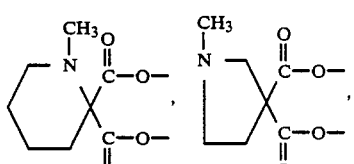

-continued
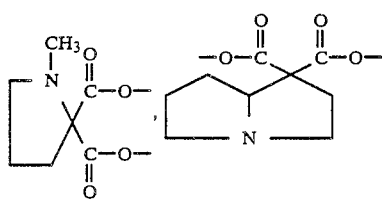
-continued
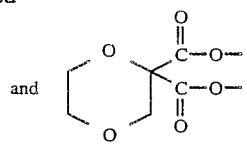
2. The compound according to claim 1, trans-(−)-[1,1-cyclobutanedicarboxylato(2-)-O,O$^1$](1,2-cyclohexanediamine-N,N′)[sulfinylbis[methane]-S]platinum.
* * * * *